(12) United States Patent
Kraemer et al.

(10) Patent No.: US 12,396,891 B2
(45) Date of Patent: *Aug. 26, 2025

(54) LASER APPARATUS FOR TREATMENT OF A CATARACTOUS LENS

(71) Applicant: Light Matter Interaction Inc., Toronto (CA)

(72) Inventors: Darren Kraemer, Toronto (CA); Michael Cowan, Toronto (CA)

(73) Assignee: Light Matter Interaction Inc., Toronto (CA)

( * ) Notice: Subject to any disclaimer, the term of this patent is extended or adjusted under 35 U.S.C. 154(b) by 259 days.

This patent is subject to a terminal disclaimer.

(21) Appl. No.: 18/295,497

(22) Filed: Apr. 4, 2023

(65) Prior Publication Data

US 2023/0240894 A1 Aug. 3, 2023

Related U.S. Application Data

(63) Continuation of application No. 17/104,522, filed on Nov. 25, 2020, now Pat. No. 11,648,150, which is a (Continued)

(51) Int. Cl.
| | |
|---|---|
| *A61F 9/008* | (2006.01) |
| *A61B 5/00* | (2006.01) |
| *A61B 17/00* | (2006.01) |
| *A61B 18/00* | (2006.01) |
| *A61B 18/22* | (2006.01) |
| *A61B 34/20* | (2016.01) |

(Continued)

(52) U.S. Cl.
CPC .......... *A61F 9/00825* (2013.01); *A61B 18/22* (2013.01); *A61F 9/00736* (2013.01); *A61F 9/00834* (2013.01); *A61B 5/0075* (2013.01); *A61B 2017/00115* (2013.01); *A61B 2017/00172* (2013.01); *A61B 2018/00303* (2013.01); *A61B 2018/00642* (2013.01); *A61B 2018/00666* (2013.01); *A61B 2018/00708* (2013.01); *A61B 2018/00791* (2013.01); *A61B 2018/2205* (2013.01); *A61B 2018/2255* (2013.01); *A61B 2034/2048* (2016.02); *A61B 2090/3979* (2016.02); *A61B 2218/002* (2013.01); *A61B 2218/007* (2013.01); *A61F 2009/0087* (2013.01); *A61F 2009/00887* (2013.01)

(58) Field of Classification Search
None
See application file for complete search history.

(56) References Cited

U.S. PATENT DOCUMENTS

| | | |
|---|---|---|
| 5,151,098 A | 9/1992 | Loertscher |
| 5,738,677 A | 4/1998 | Colvard et al. |

(Continued)

FOREIGN PATENT DOCUMENTS

| | | |
|---|---|---|
| EP | 0770370 A2 | 2/1997 |
| WO | 0189437 A2 | 11/2001 |
| WO | 2006069448 A2 | 7/2006 |

*Primary Examiner* — Carl H Layno
*Assistant Examiner* — Manolis Pahakis
(74) *Attorney, Agent, or Firm* — Smart & Biggar LP

(57) ABSTRACT

An apparatus for aiding the removal of cataracts in which an optical fiber delivers sufficient optical energy of the correct wavelength, pulse duration to achieve controlled non-thermal and non-acoustic dissolution of hard cataract tissue.

10 Claims, 9 Drawing Sheets

Related U.S. Application Data continuation of application No. 15/512,129, filed as application No. PCT/CA2015/050915 on Sep. 18, 2015, now Pat. No. 10,881,551.

(60) Provisional application No. 62/052,109, filed on Sep. 18, 2014.

(51) Int. Cl.
*A61B 90/00* (2016.01)
*A61F 9/007* (2006.01)

(56) References Cited

U.S. PATENT DOCUMENTS

| | | | |
|---|---|---|---|
| 6,156,030 A * | 12/2000 | Neev | B23K 26/53 |
| | | | 433/29 |
| 6,544,254 B1 | 4/2003 | Bath | |
| 7,824,870 B2 * | 11/2010 | Kovalcheck | A61B 18/14 |
| | | | 435/285.2 |
| 10,588,694 B1 * | 3/2020 | Neev | A61B 18/203 |
| 10,702,338 B2 * | 7/2020 | Shazly | G02B 26/04 |
| 2001/0046132 A1 * | 11/2001 | Lanzetta | A61F 9/00821 |
| | | | 362/802 |
| 2004/0158236 A1 | 8/2004 | Thyzel | |
| 2005/0197655 A1 | 9/2005 | Telfair | |
| 2006/0100613 A1 | 5/2006 | McArdle et al. | |
| 2006/0153254 A1 * | 7/2006 | Franjic | G02F 1/39 |
| | | | 372/30 |
| 2006/0195072 A1 | 8/2006 | Miller | |
| 2007/0055221 A1 * | 3/2007 | Lubatschowski | A61F 9/008 |
| | | | 606/5 |
| 2007/0185475 A1 | 8/2007 | Frey et al. | |
| 2009/0137993 A1 | 5/2009 | Kurtz et al. | |
| 2010/0213367 A1 * | 8/2010 | Miller | G01N 1/405 |
| | | | 436/175 |
| 2010/0324543 A1 | 12/2010 | Kurtz et al. | |
| 2011/0106102 A1 | 5/2011 | Balicki et al. | |
| 2012/0116372 A1 | 5/2012 | Degani et al. | |
| 2013/0035676 A1 * | 2/2013 | Mitchell | A61B 18/22 |
| | | | 606/16 |
| 2014/0194859 A1 | 7/2014 | Ianchulev | |
| 2015/0157505 A1 | 6/2015 | Neev | |
| 2015/0342678 A1 * | 12/2015 | Deladurantaye | A61F 9/008 |
| | | | 606/5 |
| 2018/0214210 A1 * | 8/2018 | Mitchell | A61B 18/22 |

* cited by examiner

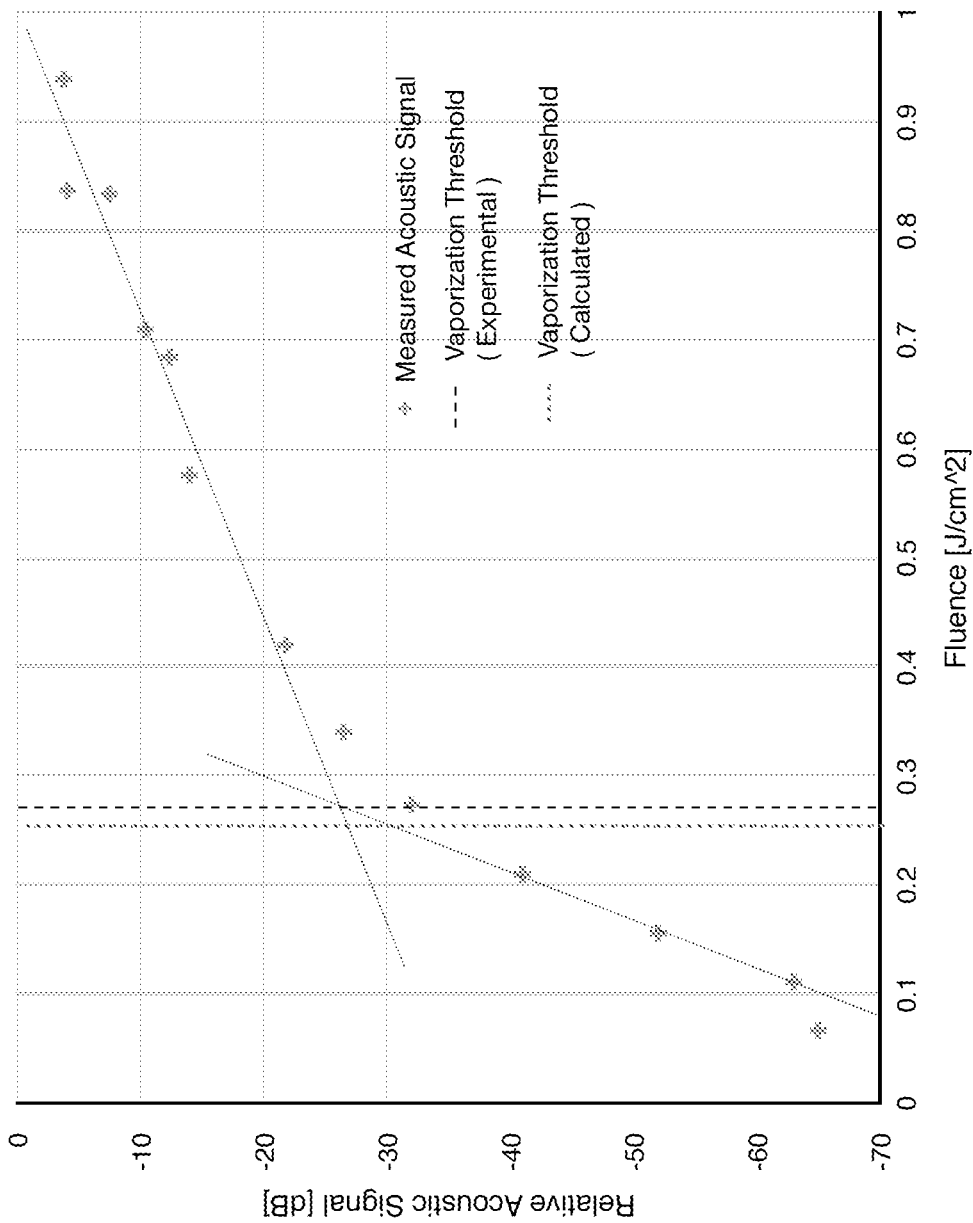

LASER APPARATUS FOR TREATMENT OF A CATARACTOUS LENS

CROSS-REFERENCE TO RELATED APPLICATIONS

The present application is a continuation U.S. patent application Ser. No. 17/104,522, granted as U.S. Pat. No. 11,648,150; which is a continuation of U.S. patent application no. 15/512,129, granted as U.S. Pat. No. 10,881,551; which is a national stage application, filed under 35 U.S.C. § 371, of International patent application no. PCT/CA2015/050915; which claims priority from U.S. provisional patent application No. 62/052,109, filed Sep. 18, 2014; the entireties of which are all hereby incorporated by reference.

FIELD

The present disclosure relates to methods and apparatuses for delivery of laser radiation for therapeutic purposes directed to and within a cataractous lens.

BACKGROUND

A cataract is a clouding of the lens of the eyes which prevents clear vision. Although most cases of cataract are related to the aging process, occasionally children can be born with the condition, or a cataract may develop after eye injuries, inflammation and some other eye diseases. Treatment for chronic deterioration of lens tissues is one of the most frequently performed surgeries.

In conventional cataract surgery, the eye surgeon typically uses a hand-held metal or diamond blade to create an incision in the area where the sclera meets the cornea. The next step for the cataract surgery is typically to remove the front portion of the capsule to allow access to the cataract. Once the capsule is opened a tool can be inserted to break apart and disrupt the cataract prior to removal. Tools for breaking apart the lens include mechanical tools such as scalpels or forceps to tear the tissue apart, and more recently tools containing ultrasonic transducers have been used to emulsify tissue prior to aspiration. Even more recently, devices have been proposed that use laser radiation to break-down tissue through heating effects or acousto-optically generated ultrasonic energy for phacoemulsification (an example is described in U.S. Pat. No. 6,083,192). Most recently, techniques have been adopted in which radiation from very short pulsed lasers that are not absorbed well in eye tissue are focused inside the volume of the cataractous lens to achieve photo-disruption of the tissue prior to aspiration.

However, conventional approaches may have one or more shortcomings. Using only mechanical tools, it is usually difficult and time consuming to carefully tear the lens tissue apart without creating uncontrolled stresses in the adjacent tissue, such as tearing of the capsule.

Ultrasound tools used for the phacoemulsification technique are usually able to effectively and quickly disintegrate hard lens tissue prior to aspiration. Ultrasonic energy however typically exerts negative effects on the tissues, including mechanical, thermal and non-thermal effects. Thermal effects are caused by the conversion of ultrasonic energy into thermal energy. This can result in heating or burning of the cornea. The ultrasound is essentially a high frequency mechanical perturbation of the tissue which disrupts the lens structure. This however is accompanied by acoustic cavitation of the tissue and the resultant shock waves which can propagate and further perturb tissue centimeters away from the transducer. Furthermore, the ultrasonic formation of free radicals during the cavitation process can damage delicate endothelial cells on the back surface of the cornea with oxidative stress. Ultrasonic energy propagates very well in aqueous tissue and the use of too much ultrasonic energy can lead to significant undesirable complications in parts of the eye beyond the lens, such as the cornea and retina.

Conventional devices which use laser radiation to generate the ultrasonic energy typically suffer from the same limitations. Such approaches typically involve coupling pulsed laser light into the lens tissue using fiber optics for the purpose of ionizing, heating or shockwave generation by optical interaction with the tissue or some part of the tool tip. Examples are described in U.S. Pat. Nos. 4,744,360, 6,623,477, 5,843,071, 5,919,186, and 6,083,192.

With the advent of picosecond and femtosecond pulsed lasers, scientists first observed photodisruption, a different ablation mechanism in which the concentrated electromagnetic field of the short pulses destroys matter by pulling it apart on a sub-atomic level. Reacting to the strong fields, the electrons in the material become energized beyond the ionization limit (an example is described in U.S. Pat. No. 5,656,186). This mechanism is often referred to as "cold ablation" or "multi-photon ionization" and has been proven to enable extremely precise machining of many materials. Regardless, the effects of this process on biology are only recently being considered and there is concern for biological damage due to free radicals caused by exposure of tissue to this kind of ionization radiation. Picosecond and femtosecond pulsed lasers have been applied to cataract surgery. Typically the surgeon creates a precise surgical plan typically using a sophisticated 3-D image of the eye. As part of the preparatory steps for commencement of the surgery, these femtosecond laser systems are able to partially disrupt soft cataractous lenses by transmitting through the transparent portions of the eye and focusing within selected portions of the lens to segment the cataract into smaller pieces, with the goal of reducing or eliminating the use of ultrasound energy for lens disruption, and thereby reduce the risk of burning and distorting the incision in the cornea. Using the fs laser in this step may reduce the required phacoemulsification time, but fs radiation is not innocuous; and typically does not transmit consistently with unclear or scattering tissues in the beam path before the focus inside the lens. Furthermore, in most practical applications other than very soft cataracts, additional phacoemulsification is needed to break-up the remaining lens tissue. An example is described in U.S. Patent Application Publication No. 2009/0137993.

SUMMARY

In some examples, the present disclosure provides a laser-operated apparatus and technique for disruption of cataractous-lens tissue prior to removal.

In various examples of the present disclosure, impulsive heat deposition is utilized to achieve micro-disruption of the lens tissue while reducing or minimizing propagation of the energy to tissues other than cataractous-lens. This may be achieved by providing a tool which can be inserted within the volume of the cataract while providing suitable conditions for impulsive heat deposition upon contact with the distal end of the tool.

In some examples, the present disclosure provides an instrument which embodies its own means of irrigation and aspiration of liquid at the site of the fragmentation, without interfering with or diminishing the effectiveness of the phacoablation.

In some examples, the present disclosure provides a surgical instrument which enables external manipulation of the output end of an optical fiber inside the eye, which may be directed only on nearby cataractous lens tissue to be fragmented. The particular laser that emits from the fiber tip is selected for its wavelength, intensity and pulse duration which may achieve conditions suitable for rapid micro-disruption through impulsive heat deposition.

In some examples, the present disclosure provides an apparatus for disruption of cataracts in lens tissue. The apparatus includes: a source of pulsed laser radiation, the source being controllable to select a pulsing rate of the pulsed laser radiation; an optical waveguide configured to transmit the pulsed laser radiation from the source, the optical waveguide being coupleable to the source at a proximal end of the optical waveguide to receive the pulsed laser radiation from the source; the pulsed laser radiation being controlled to exhibit conditions at a distal end of the optical waveguide such that the light intensity which exits the optical waveguide is sufficient to produce microdisruption of the lens tissue by impulsive heat deposition, the conditions including: a wavelength in the range of about 2700 nm to about 3300 nm, the wavelength being selected to match an absorption peak of at least one component of the lens tissue; wherein the wavelength causes the pulsed laser radiation to produce laser pulses having an energy sufficient to cause, when the laser pulses are absorbed in a volume of the material irradiated by the laser pulses, superheated temperatures above a vaporization point of the at least one component of material contained in the laser irradiated volume; a pulse duration time in the range of about 10 ps to about 1 ns, the pulse duration time being selected such that each pulse duration time is shorter than a time required for thermal diffusion out of the laser irradiated volume and shorter than a time required for a thermally driven expansion of the laser irradiated volume; wherein the combination of selected pulse duration time and selected pulse energy is low enough to result in a peak intensity of each laser pulse below a threshold for ionization-driven ablation to occur in the irradiated material; and wherein the conditions are selected to result in conversion of a majority of the energy contained in each laser pulse to ablation of the material in the volume with any residual energy being insufficient to substantially damage material surrounding the volume irradiated by the pulsed laser.

BRIEF DESCRIPTION OF THE DRAWINGS

Reference will now be made, by way of example, to the accompanying drawings which show example embodiments of the present application, and in which:

FIG. 9 is a chart showing example experimental measurements of ablation threshold.

Similar reference numerals may have been used in different figures to denote similar components.

DESCRIPTION OF EXAMPLE EMBODIMENTS

Figure 1:
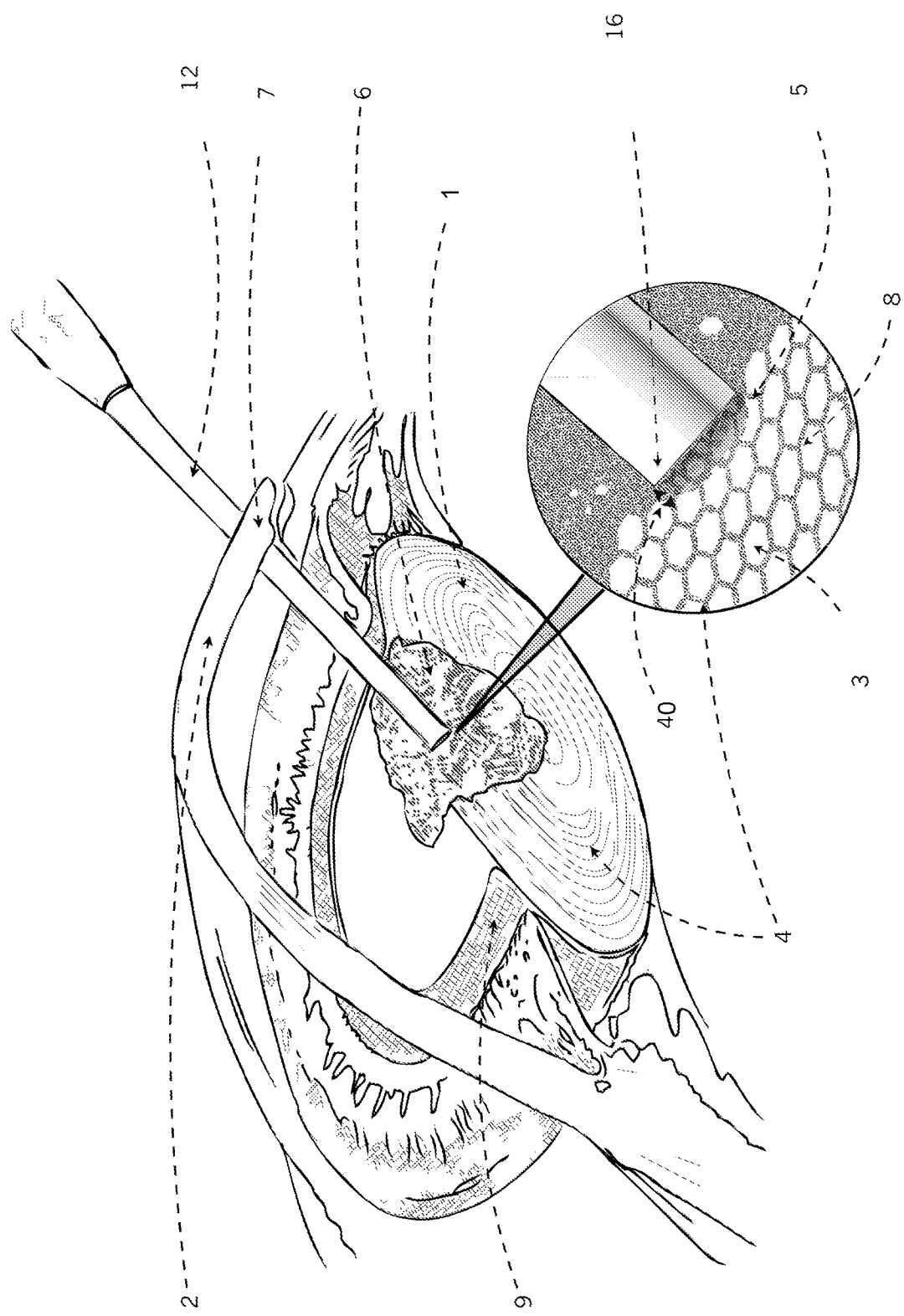
FIG. 1 illustrates an example procedure for micro-disruption of cataracts lens tissue, in accordance with an example of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. Although the present disclosure describes certain equations and/or theories to aid in understanding, the present disclosure is not necessarily bound to any of the described equations and/or theories.

Nanosecond and longer pulsed mid-IR lasers have been used for ablation of ocular tissue such as cornea, however conventionally it had been widely considered best practice to avoid the use of pulse durations shorter than a nanosecond to avoid the potential of ionization effects (see, for example, H. J. Hoffman, W. B. Telfair, "Minimizing thermal damage in corneal ablation with short pulse mid-infrared lasers" *J. Biomed. Opt.* 4.4 (1999): 465). A mechanism for laser ablation, using impulsive heat deposition, was described in U.S. Pat. No. 8,029,501 (which is hereby incorporated by reference in its entirety) in which rapid-heating by excitation of vibrational modes inside of tissue causes vaporization of the exposed tissue. This has been shown in a number of studies to display unique laser material removal properties. However, applications of this cutting mechanism to cataract surgery have been limited due to the strong absorption in the eye tissue which limits operation to surface tissue.

In contrast to some of the previous solutions discussed above, in various examples of the present disclosure, the laser ablation occurs inside the body with the fiber tip surrounded by and in contact with tissue and fluid in the eye. There is no free surface for ablated tissue to expand into. Instead, the hard lens tissue is disrupted and the small fragments are dispersed into the surrounding fluid in the eye.

In various examples, the present disclosure provides a cataract removal system that may avoid the energy propagation issues of the phacoemulsification process, photoacoustic laser based systems.

In some examples, the present disclosure describes an apparatus including a laser probe which, on contact, and internal to the body, can efficiently drive rapid dissolution of lens tissue by optical excitation of selected vibrational modes inside of the tissue's molecules on timescales faster than heat diffusion to the surroundings. In some examples, the present disclosure describes an approach for efficiently disrupting hard cataract tissue while avoiding the issues of energy propagation into other tissue's of the eye. In some examples, the present disclosure may provide one or more advantages over the conventional approach in respect efficient disruption of very hard lens material, such as one or more of: less thermal or acoustic energy exposure to adjacent tissue, with or without an adjacent free surface; delivery through a fiber optic probe with sizes possibly down to the hundred micro size; and avoidance of tissue ionization and oxidative stress due to free-radical formation.

FIG. 1 shows an example illustration of micro-disruption of cataracts lens tissue 1. In the example shown, micro-disruption of the cataractous lens tissue 1 occurs when laser pulses of a certain duration, wavelength and pulse energy, are coupled into an optical waveguide 12 and exits (at a light exit) from the distal end 16 of the optical waveguide 12, where the distal end 16 has been inserted at some point 7, into the eye and directed inside of the ocular lens 1. The light emitted from the distal end 16 is strongly absorbed by vibrational modes of the exposed molecules of the lens cells 3 and/or intercellular regions 8, that are in contact with the light exit of the waveguide 12 or within a distance close to the optical absorption depth 40 of the laser light inside the tissue 1. The optical absorption depth 40 is a measurement of the extent to which the laser light is absorbed by tissue and/or fluid in the vicinity of the distal end 16. The optical absorption depth 40 may be dependent on the parameters of the laser light and/or the optical properties of the tissue and/or fluid surrounding the distal end 16. The cells 3 and/or intercellular regions 8 that are exposed to the emitted light together may be referred to as the irradiated volume 5. The result is micro-disruption of the lens cells 3 and/or the cell structure 4 of the lens 1 faster than thermal diffusion or shockwave propagation outside the irradiated volume 5. The excited molecules result in effective dissolution 6 of the hard cataract lens 1 in such a way that the energy typically neither heats surrounding tissue, nor ionizes the excited tissue, and typically prevents propagation of the energy to distant parts of the eye such as the cornea 2 and/or the lens capsule 9. Operation of the example waveguide 12 is further explained below.

Recently discovered molecular dynamic behavior of water molecules, in solution or bound to proteins and other molecules that comprise living tissue, present a pathway to a laser-tissue interaction that is different from prior mechanisms of mechanical, acoustic, or laser induced breakdown, and that may provide advantages over conventional approaches. Example conditions suitable to produce this effect are provided in the present disclosure. The selected combination, as discussed in greater detail below, of short pulse duration, wavelength and pulse energy, pulse repetition frequency is delivered at the distal end of an optical waveguide.

Figure 2:
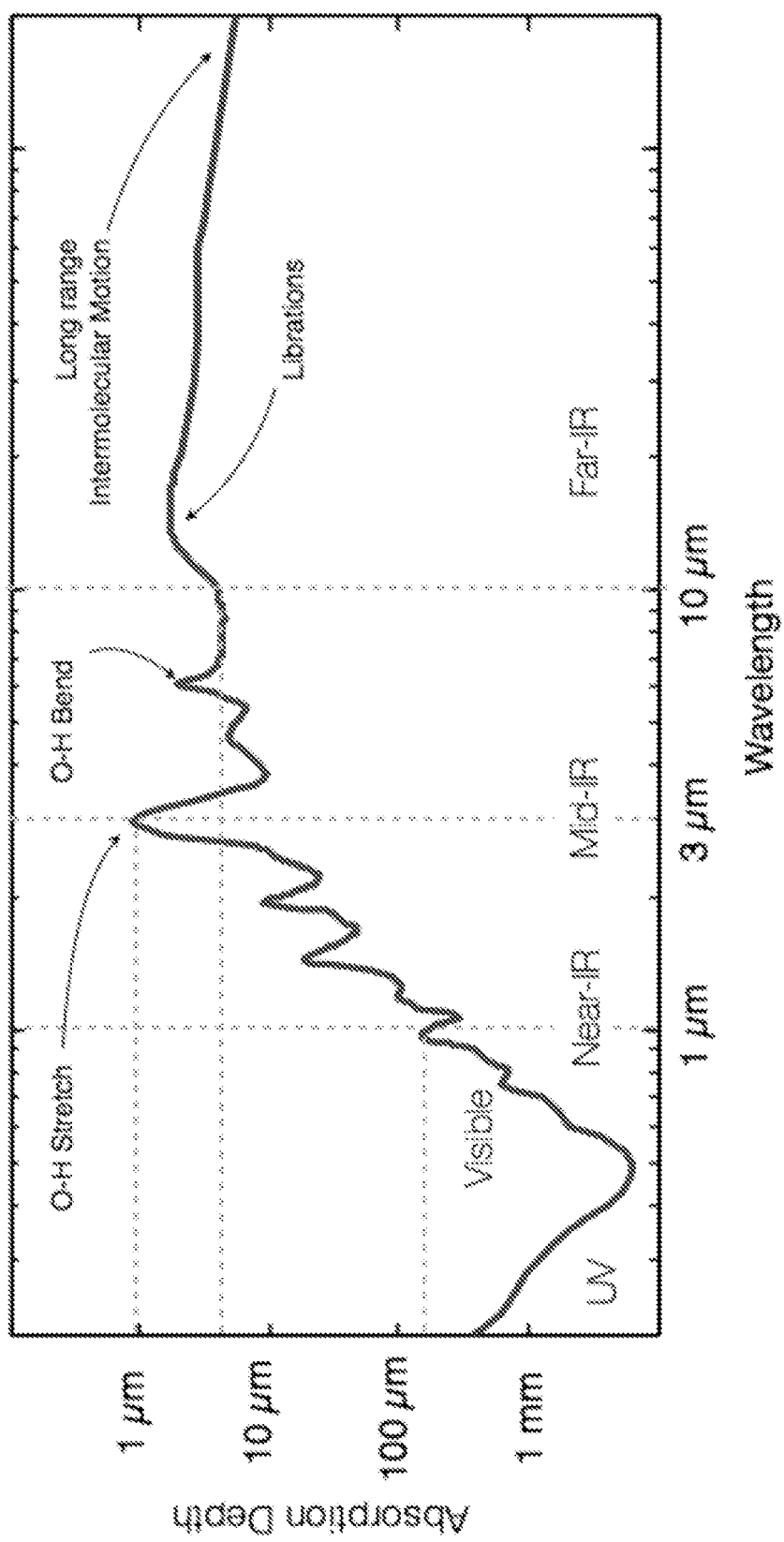
FIG. 2 shows the absorption spectrum of water from visible to far infrared (IR)

The wavelength of the laser radiation should be strongly absorbed in the tissue, by transfer to vibrational modes. By targeting a strong peak in the vibrational spectrum, such as the ubiquitous OH-stretch region of $H_2O$, the vibrational modes may quickly absorb the electromagnetic radiation and may effectively localize optical energy to micron scale deep sections of the exposed tissue. This is illustrated by FIG. 2, which shows the absorption spectrum of water from visible to far-IR. The maximum absorption occurs around 3000 nm where a broad peak corresponds to the OH-stretching vibrational modes of liquid water molecules between about 2700 and 3300 nm. The spectrum also shows the resonance conditions between the OH-stretch and other vibrational modes such as the OH bend and Intermolecular modes. Other absorption peaks, for example around the OH-bend at about 6000 nm, may also be used. In examples disclosed herein, the broad OH-stretch peak, in the range of about 2700 nm to about 3300 nm, particularly around 3000 nm, are used since it may be more effective and/or practical to produce laser light at this wavelength range. Generally, in order for the ablation mechanism described herein to be effective, the laser light should be selected to match a strong absorption wavelength of water or the tissue.

Subsequently, wavelengths in the mid infrared have an increased threshold for photo-ionization effects due to their lower photon energies compared to near-IR, visible or UV lasers. Ionization of tissue, a mechanism that has its own intensity threshold for photo-disruption, is an undesirable consequence which may be avoided by examples of the present disclosure. The mechanism described herein typically cannot be achieved at lower wavelengths, for example below about 1500 nm, where the multi-photon ionization occurs at thresholds lower than the requirements for micro-disruption through vibrational excitation of the material.

The pulse duration of the laser radiation should also be carefully selected, as it dictates the minimum timescale at which energy is absorbed and redistributed. Slow mechanisms of energy redistribution from optical excitation include thermal diffusion (many nanosecond timescales) and shockwave emission (timescale>1 ns) that occur on timescales orders of magnitude slower than fast mechanisms of energy redistribution such as avalanche ionization and vibrational redistribution that occur on the femto-picosecond timescale (see, for example Rafael R. Gattass & Eric Mazur, Femtosecond laser micromachining in transparent materials. Nature Photonics 2, 219-225 (2008)). The rate of transfer of excited energy between vibrational modes in the presence of water occurs on a particularly fast timescale compared to other molecules (typically femtosecond to picosecond timescale) due to strong resonant coupling with lower frequency vibrational modes in the solvent. If the volume of excited tissue is large enough, e.g. micron scale, the time required for diffusion of temperature or pressure gradients is much larger than the time required for those same gradients to disrupt the cellular structure of the tissue. In other words, this micro-disruption is a process in which electromagnetic radiation drives the intra-molecular vibrations of the molecules in the tissue that quickly and efficiently achieve molecular rearrangement (without photo-ionization) and ultimately cellular scale mechanical motions faster than the energy can escape the irradiated volume as heat or shockwave.

A certain amount of pulse energy must be absorbed by a given volume of tissue to achieve the non-thermal and non-acoustic micro-disruption effect. Laser pulses in the picosecond time regime may be suited for delivering the required energy to the tissue on this timescale while avoiding peak intensities that would result in ionization. If insufficient energy is delivered during the exposure of the laser pulse, the absorbed energy will dissipate as heat on thermal relaxation timescales and the micro-disruption effect will not occur. If too much energy is delivered during the given pulse duration, the electromagnetic field intensities will begin to overcome the forces binding electrons to their molecules and result in catastrophic photo-ionization of the tissue.

The micro-disruption threshold has been observed experimentally with picosecond pulses and the effects of repeated exposure to below threshold optical excitation has been found to manifest themselves as melting or burning of the tissue, whereas at above threshold optical excitation micro-disruption can be clearly observed. Above the threshold, the tissue is disrupted with little, negligible or practically no residual thermal effects.

Since the micro-disruption process may be less than 100% efficient the pulsing rate should also be considered. Individual laser pulses should have sufficient energy to drive micro-disruption while allowing time between pulses for any residual energy left behind to dissipate before the next pulse of energy arrives, so as to reduce or prevent accumulation of the residual energy sufficient to drive other mechanisms of tissue damage such as increased temperature or shock waves. Laser repetition rates in the 10-100 000 Hz range may enable average powers suitable for fast tissue disruption with sufficient time between pulses. Bursts of multiple pulses at faster repetition rates may not satisfy the criteria if sequential pulses that are below the energy threshold for micro-disruption are absorbed in the same volume at time intervals longer than the relaxation time of the excited vibrational modes.

In the case of lens tissue, this photo-mechanism is enhanced by the cellular structure of the eye in which long, thin, transparent cells, with diameters typically between 4-7 microns and lengths of up to 12 mm are trapped in a regular pattern in shell like formations around the nucleus of the lens (as described in, for example, Biological glass: structural determinants of eye lens transparency, Phil. Trans. R. Soc. B. 2011 366 1250-1264). The majority of cells comprising the lens have a flattened hexagonal structure and are aligned into regular rows. Interdigitations are evident at the edges along the length as well as at the ends of the fiber-like cells and act as an interlocking mechanism to maintain the alignment of the cellular structure, which gives the lens its transparent optical properties in the visible spectrum. In the space separating the cells, water and cell membrane proteins act to create a fluid channel for cell hydration (as described in, for example, Gutierrez D B, Garland D, Schey K L. Spatial analysis of human lens aquaporin-0 post-translational modifications by MALDI mass spectrometry tissue profiling, Exp. Eye Res., 93:912-920, 2011). By selectively exciting the water molecules between cells and those on the surface of the proteins, it is possible to unravel the interlocking structure of the lens tissue so that the cells or portions of cells are easily dissolved into the fluid of the anterior portion of the eye.

Figure 3B:
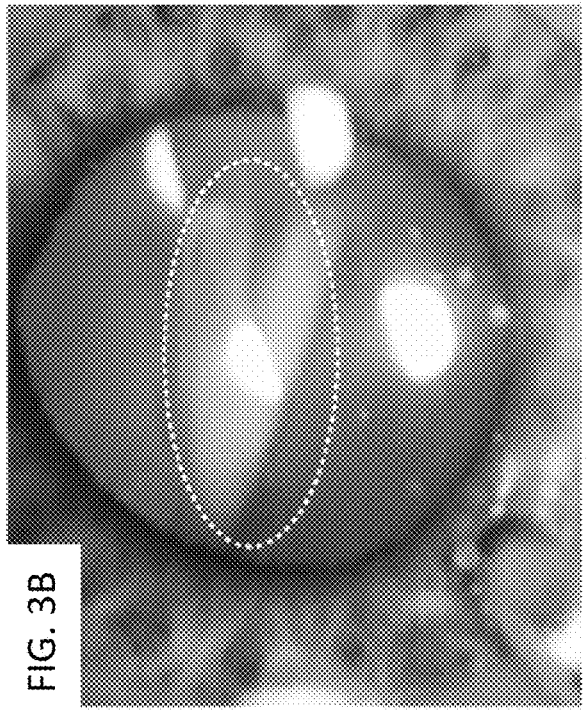
FIG. 3 shows photographs of an example micro-disruption process, in accordance with an example of the present disclosure.
Figure 3A:
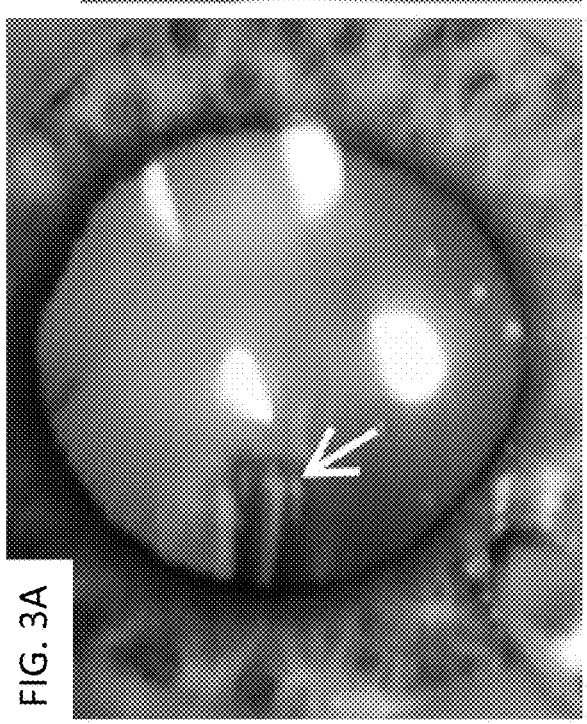
Figure 3D:
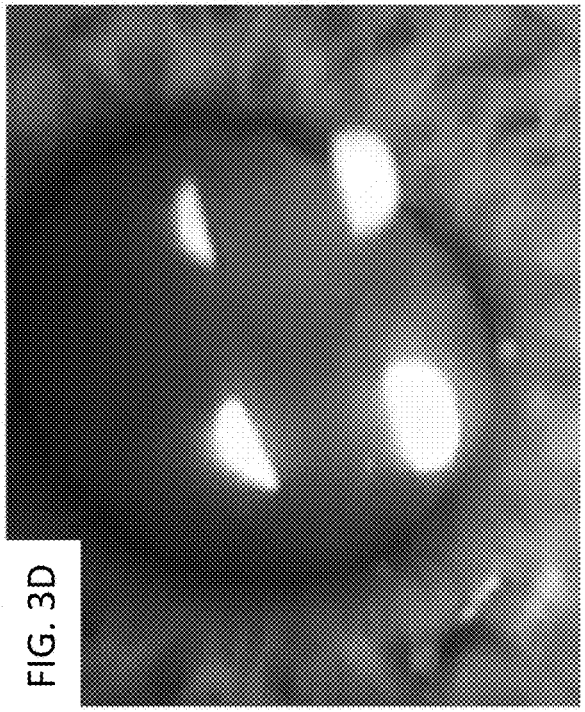
Figure 3C:
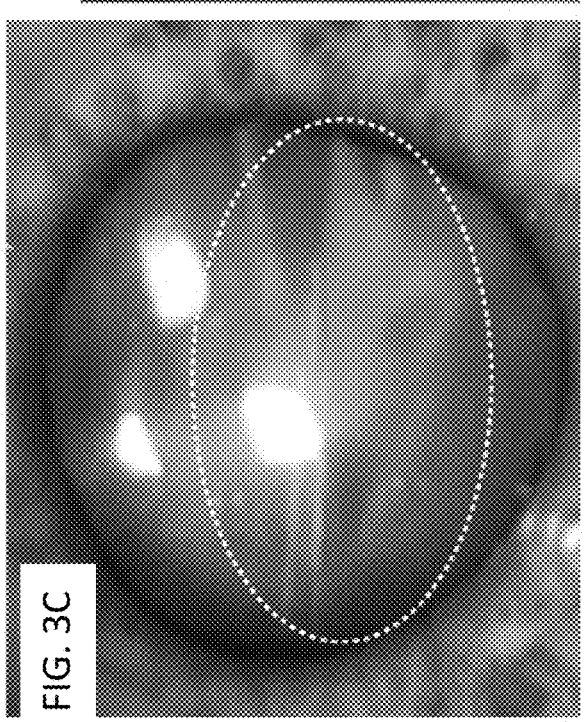

FIGS. 3A-3D show photographs of an eye while undergoing an example micro- disruption of tissue, in accordance with examples of the present disclosure. FIG. 3A shows the cataract tissue of a human eye in contact with the distal tip (indicated by white arrow) of a 0.5 mm diameter solid sapphire fiber into which pulses of 3000 nm, 400 ps, 500 uJ laser radiation energy are coupled at a pulsing rate of 1 kHz. FIGS. 3B and 3C show the visible effect after exposure to several seconds of laser radiation delivered to tissue that has come in contact with the distal tip of the fiber. The portions of the lens that were exposed through contact with the distal tip of the fiber can be seen to scatter the light (indicated by dashed ellipse) which is otherwise transmitted by neighboring tissue. FIG. 3D shows the eye after complete disruption of the anterior portions of the lens as shown by the lack of reflected light.

In some examples, a picosecond pulsed (<1 ns) laser with wavelengths corresponding to an absorption peak in the vibrational spectrum of water (around 3000 nm) and pulse energy $E_{pulse}$, is coupled into a optical waveguide or fiber optic whose output aperture has an area of A and directed inside the volume of a cataract such that the tissue which is directly in contact with the fiber tip can be exposed to light intensities $I=E_{pulse}/A$ which exceed the threshold required for micro-disruption of the targeted lens tissue. This intensity threshold may vary somewhat based on tissue characteristics, such as the tissue type and in the case of cataracts, the age and/or hardness of the cataract. A lower limit for the intensity threshold may be approximately 0.25 $J/cm^2$, as determined by experiment, example results of which are shown in FIG. 9.

FIG. 9 shows example results of a measurement of the ablation threshold using 400 picosecond pulses from a 200 micron diameter fiber submersed in pure liquid water. The acoustic signal produced by the laser's interaction with the water is plotted versus the laser fluence. A change in behavior is seen at the ablation threshold near 0.25 $J/cm^2$. A calculation of the pulse energy needed to vaporize the volume of water excited by the laser gives a similar result of 0.25 $J/cm^2$ for the ablation threshold.

The upper limit for the intensity threshold may be determined by the photo-ionization threshold, which is dependent on pulse duration. At the wavelength of about 3000 nm, the minimum pulse duration may be selected to be about 10 ps to avoid ionization effects, and the maximum pulse duration may be selected to be about ins to avoid shock wave propagation in this tissue type. For a minimum pulse duration of about 10 ps, the upper limit for the intensity threshold may be experimentally determined to be about 1 $J/cm^2$.

As an example, the fiber diameter, 2r, can be chosen to be about 0.5 mm. This fiber diameter was found in some cases to be a suitably large fiber diameter for the selected pulse energy and intensity thresholds (as discussed above). In other examples where greater laser energy is selected, a larger fiber may be used. In this example, an intensity equal to the minimum ablation threshold is chosen thus requiring, for this example, a pulse energy greater than $$E_{pulse} = I_{threshold} \times A = 0.25 \frac{J}{cm^2} \times \times (0.5/2)^2 = 491 \times 10^6 \ J$$

or approximately 0.5 mJ. In another example, the fiber diameter, 2r, could be chosen to be about 0.2 mm thus requiring a pulse energy at the light exit at the distal tip of the fiber greater than $$E_{pulse} = I_{threshold} \times A = 0.25 \frac{J}{cm^2} \times \times (0.2/2)^2 = 78 \times 10^6 \ J$$

or approximately 0.08 mJ.

The equations presented above are illustrative and are not intended to be limiting. The generalized form of this equation may be used to determine the lower limit for the pulse energy required, for any given fiber diameter. The upper energy limit may be found by experimentally determining the energy at which ionization damage occurs.

Figure 4:
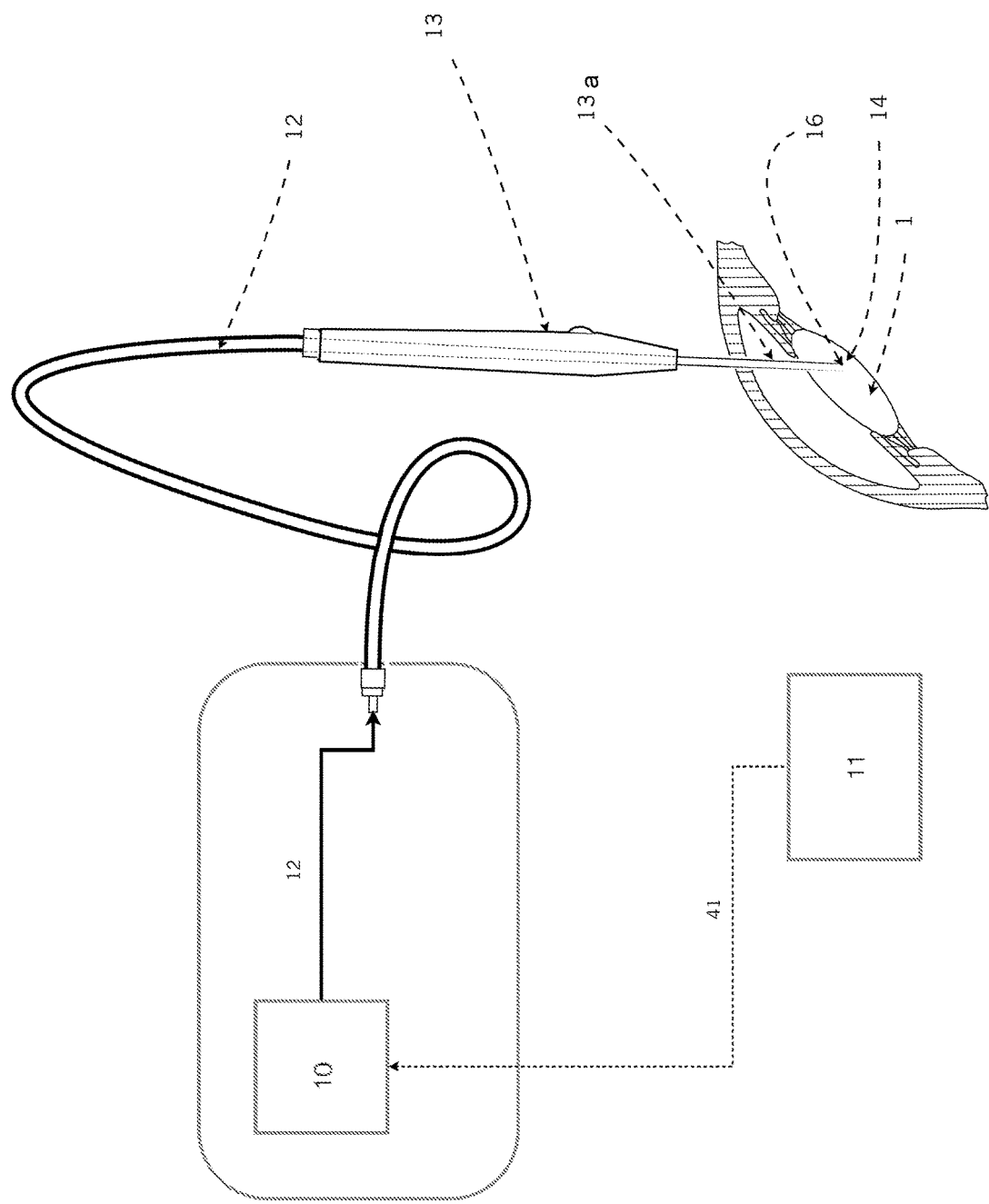
FIG. 4 is a schematic diagram illustrating an example apparatus for controlled micro-disruption of cataract tissue, in accordance with an example of the present disclosure.

FIG. 4 illustrates an example of the present disclosure. A source of laser pulses 10 is controlled by a signal 41, from a user input device 11 (e.g., a computing device, a controller or a processing unit) and a means for coupling the laser light into an optical waveguide or fiber 12. A handle or fixture 13 is provided that allows insertion and control of the distal tip 16 of the fiber 12 inside the lens portion 1 of the human eye for the purpose of cataract surgery. In some examples, a portion 13a of the apparatus that comes in contact with the tissue may be replaceable or re-useable. For example, the portion 13a of the apparatus may be a single-use assembly, or a re-useable assembly that may be detached for sterilization and re-attached for repeated use. The optical output 14 from the distal tip 16 meets the conditions necessary for controlled micro-disruption of the exposed cataract tissue, for example as discussed above.

Figure 5:
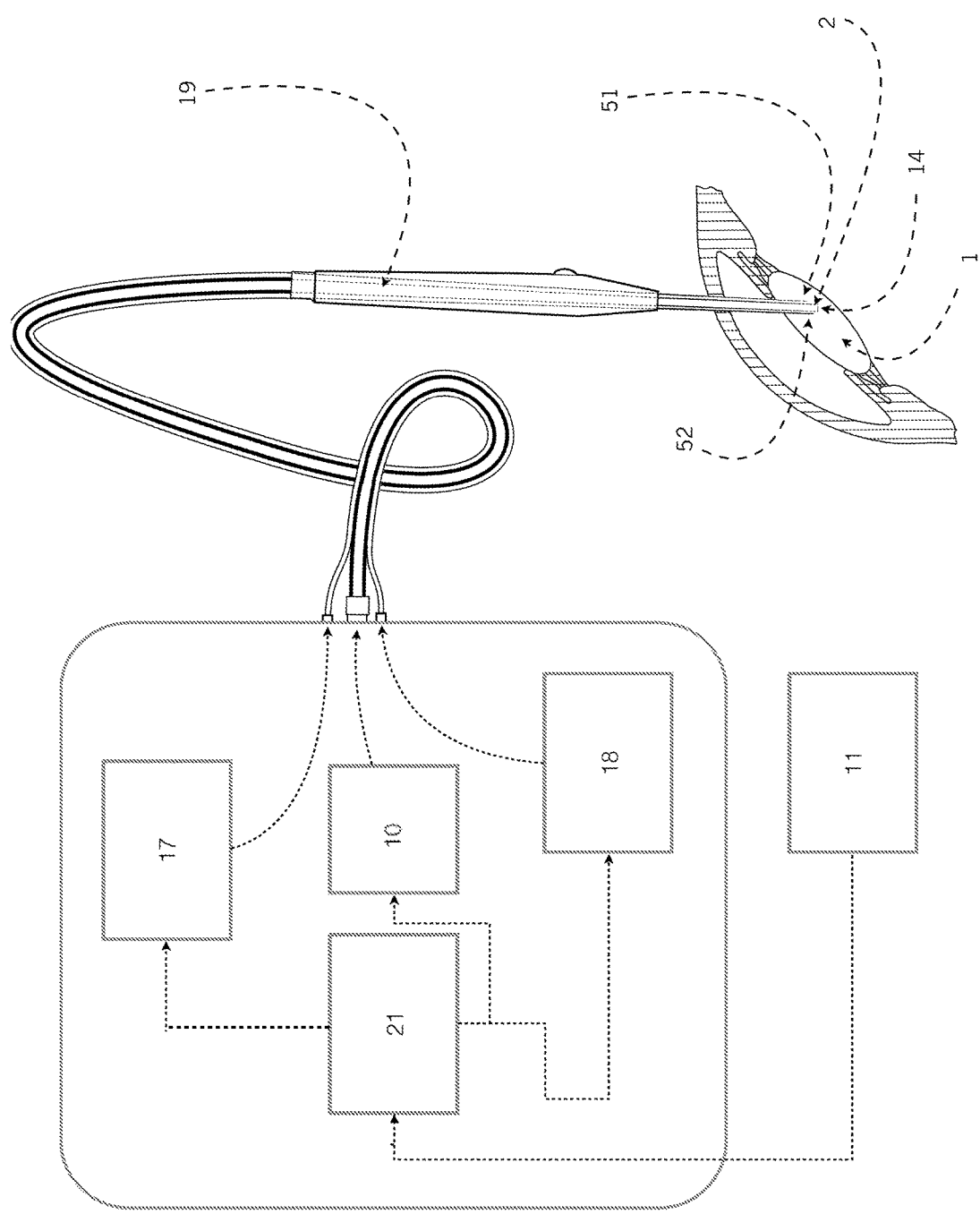
FIG. 5 is a schematic diagram illustrating another example apparatus for controlled micro-disruption of cataract tissue, in accordance with an example of the present disclosure.

FIG. 5 shows another example in which the optical fiber may be inserted directly or in combination with irrigation and or aspiration into the cataractous lens. In FIG. 5, the source of laser pulses 10 is controlled by the user input device 11 in combination with a means of irrigation 17 and a means of aspiration 18 (which are in turn also controlled by the input device 11, via a control circuit 21, for example). The source of laser pulses 10, the irrigation means 17 and the aspiration means 18 are coupled into a flexible, detachable, re-useable or disposable tool assembly 19 that allows insertion and control of the distal tip 20 of the tool assembly inside an ocular lens 1 to achieve controlled micro-disruption of the cataract tissue at the distal tip 20, as described above. One or more output channels for irrigation 51 and one or more input channels for aspiration 52 accompany the fiber optic distal tip 16 to the disrupted lens material, which can be irrigated and/or aspirated in a controlled manner with little or no loss or sudden change of intraocular pressure.

In another example, the laser output may be controlled by a controller executing an algorithm which receives inputs from one or more sensors monitoring variables such as the position and angle of the distal tip of the fiber, back scattered light emitting from the proximal end of the fiber, mechanical feedback (e.g., using a force sensor), acoustic and/or thermal conditions at or near the distal end of the fiber. The control algorithm may attempt to prevent accidental damage to surrounding tissues by shutting off the laser, when inputs from the one or more sensors indicate that surrounding tissues may be damaged. For example, one or more sensors may sense a temperature indicative of possible tissue damage (e.g., temperatures above a preset threshold). Other sensors, such as optical spectroscopic sensors or mass spectroscopic sensors may also be used to detect possible tissue damage. The one or more sensors may also sense position of the distal tip 16 (e.g., using accelerometers or other suitable position sensors, such as 3D infrared tracking) to detect whether the distal tip is outside the expected ablation area. Generally, the sensor(s) may send appropriate signal(s) to the controller whenever the sensor(s) detects that conditions (e.g., temperature, distal tip position, etc.) indicate a possible risk of tissue damage, and the controller may shut off the laser accordingly. The preset threshold(s) for the sensor(s) to indicate possible risk may be preset to be lower than the threshold value(s) at which actual tissue damage will occur, to factor in a safety margin.

In some examples, the control algorithm may be supplied with a 3D map of the boundaries of the lens (e.g., from prior imaging of the lens), enabling the controller to monitor the position of the tip and turn off the laser outside of the predetermined lens boundaries so as to avoid damage to surrounding tissues such as the capsule which should not be disrupted or removed.

Figure 6:
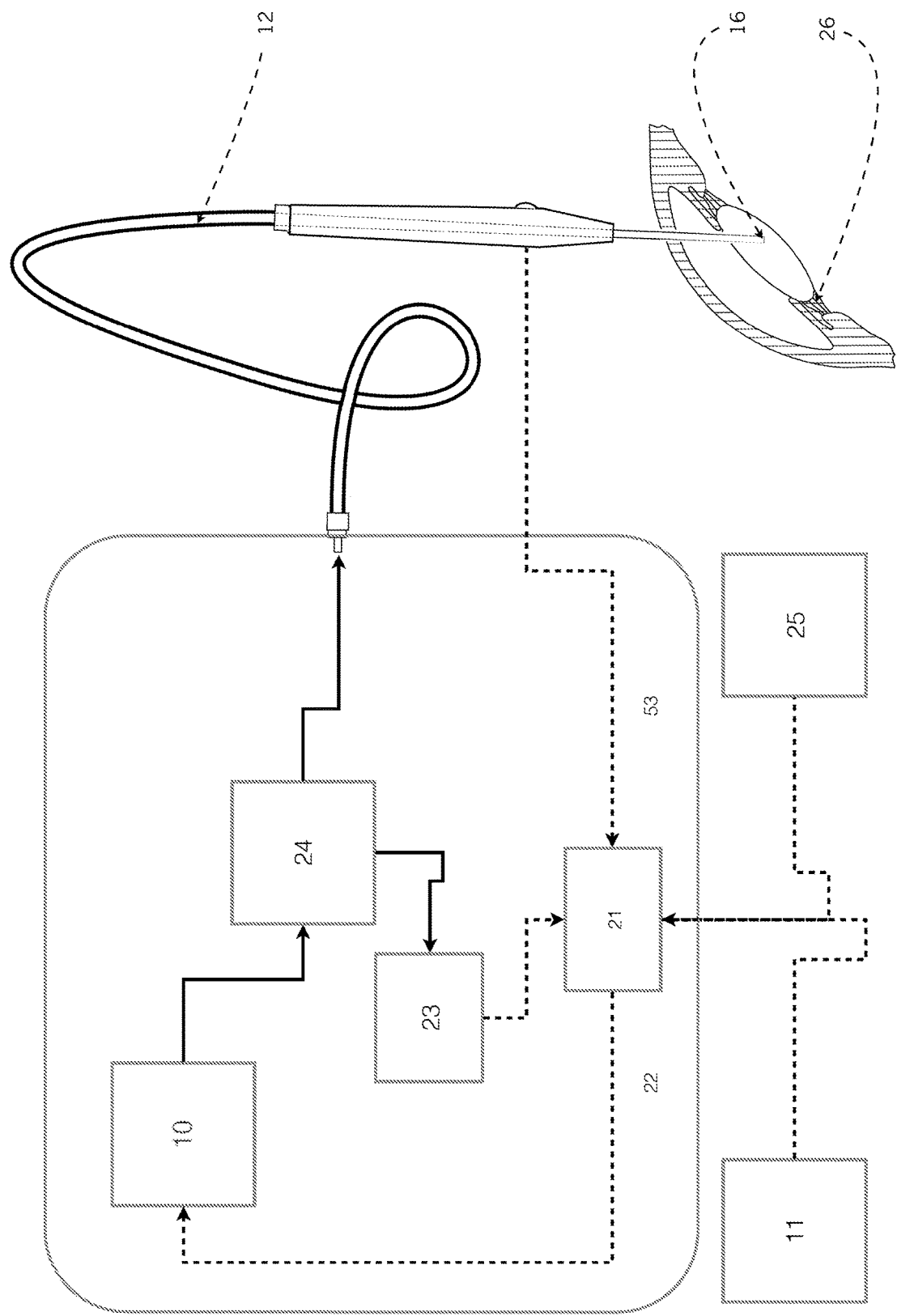
FIG. 6 is a schematic diagram illustrating another example apparatus for controlled micro-disruption of cataract tissue, in accordance with an example of the present disclosure.

FIG. 6 shows an example including the use of sensors as described above. The source of laser pulses 10 is controlled by a signal 22 from a control circuit 21 (e.g., implemented in a controller, such as a computing device) which receives inputs from one or more sensors monitoring variables such as a signal 53 (e.g., from a position and/or orientation sensor, such as an accelerometer) indicating the position and angle of the distal tip 16 of the fiber, back scattered light emitting from the proximal end of the fiber (e.g., detected by an optical sensor 23 connected by a directional or wavelength dependant means 24 of coupling light into the optical fiber 12), a mechanical feedback signal (e.g., from a force sensor), and signals indicating acoustic and/or thermal conditions at or near the distal end 16 of the fiber 12. When the control circuit 21 determines that the received signals from one or more sensors indicate surrounding tissues 26 may be accidentally damaged, the control circuit 21 shuts off the laser to the fiber 12. The control circuit 21 may also receive inputs, such as including a 3D map 25 of the boundaries of the lens (e.g., acquired in advance by a suitable imaging technique) which allows the control circuit 21 to compare the position of the tip 16 (e.g., as indicated by the position and/or orientation signal 23) with a preset boundary defined in the 3D map 25, and prevent emission of the laser light at positions outside of the predetermined boundaries so as to avoid accidental damage to surrounding tissues 26.

Figure 7:
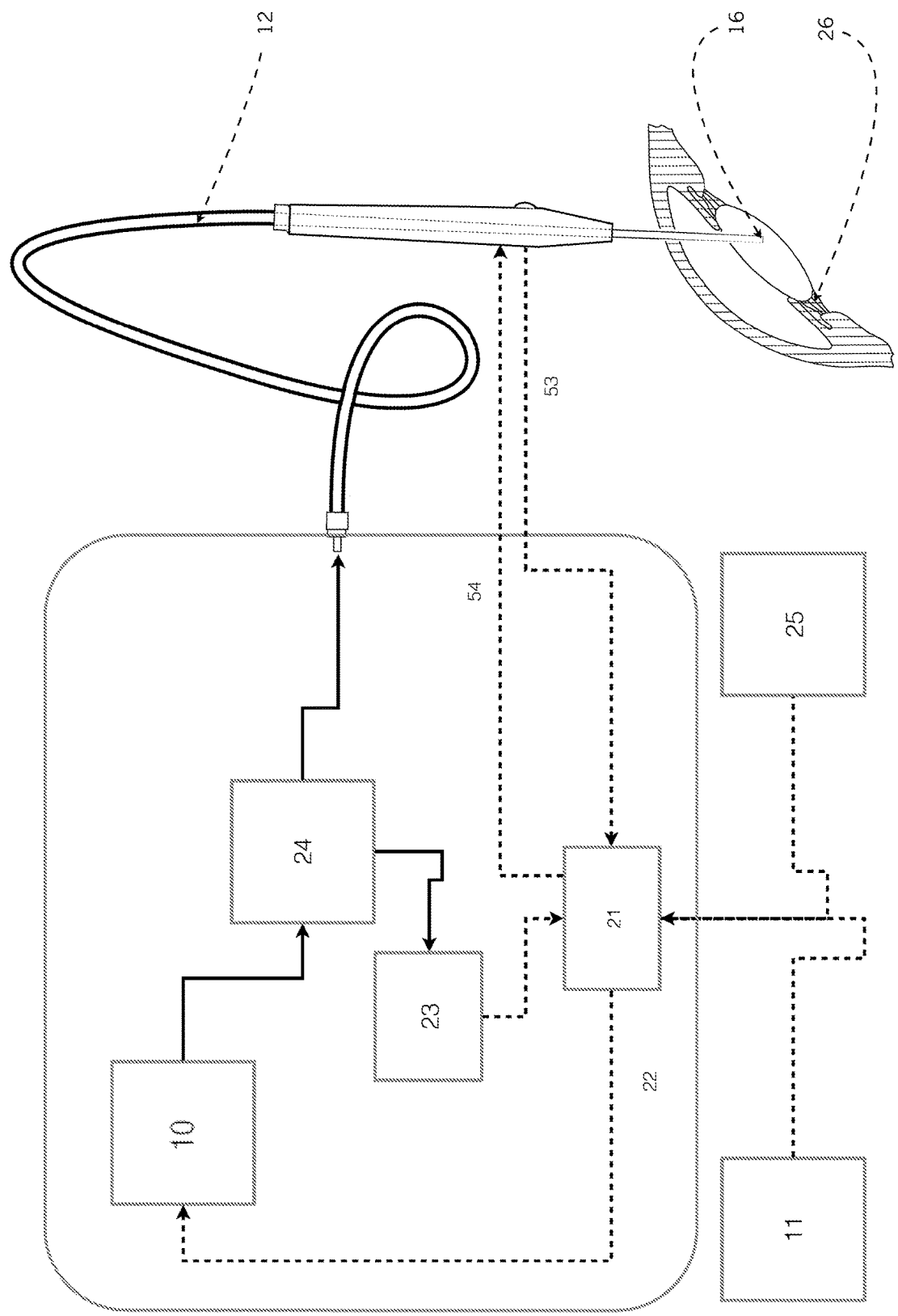
FIG. 7 is a schematic diagram illustrating another example apparatus for controlled micro-disruption of cataract tissue including user feedback or positional control, in accordance with an example of the present disclosure.

In some examples, as shown in FIG. 7, the control algorithm implemented by the control circuit 21 may also supply a control signal 54 to an actuator (e.g., a motor) of the handle or fixture of the fiber assembly to control the position of the distal tip 16 and/or provide feedback to the user in some way (e.g., tactile, audio or visual feedback). Similar to that described above, the location of the distal tip 16 of the fiber 12 is monitored (e.g., using a position and/or orientation sensor that provides a position and/or orientation signal 53 to the control circuit 21) and the position of the distal tip 16 is restricted to a predetermined volume which contains the lens material, so as to avoid accidental exposure of surrounding tissues 26 (such as the capsule which should not be disrupted or removed) to laser radiation.

In some examples, the fiber is made of a relatively hard IR transmitting material, such as sapphire (other suitable materials may include diamond, ZBLAN, YAG, etc.), and may have a tapered, curved or angled tip or any combination thereof, which may enhance the ease of use during the cataract disruption procedure.

Figure 8:
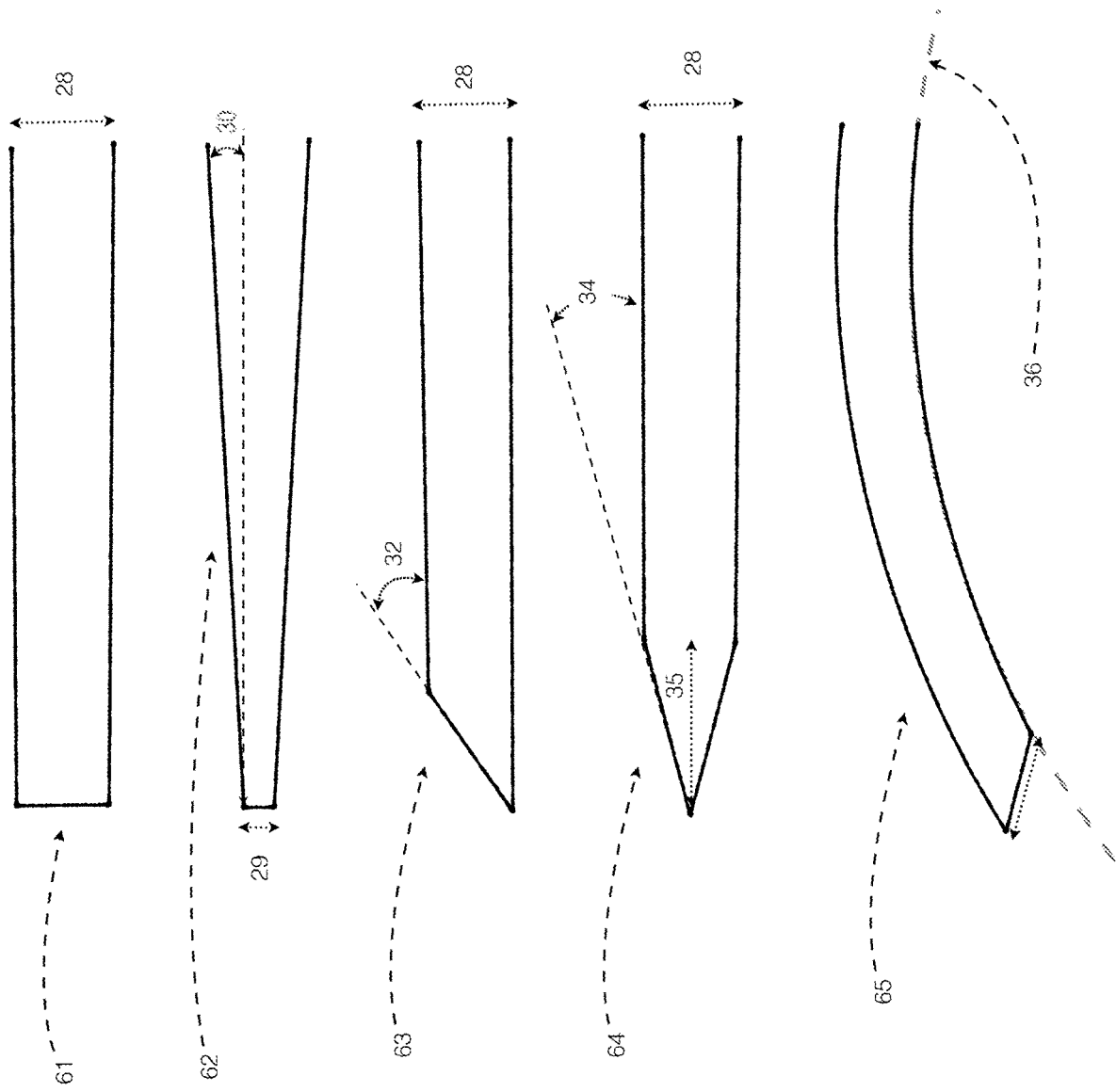
FIG. 8 shows various example geometries for the output face of the fiber in example apparatuses for micro-disruption of cataract tissue, in accordance with examples of the present disclosure.

FIG. 8 shows various example geometries for the output face at the distal tip of the fiber. Some conditions which may be imposed by these geometries on pulse energy requirements to achieve the threshold of selective micro-disruption are discussed below.

In the case of a cylindrical waveguide 61 with parallel walls and a diameter 28 of 2r the required pulse energy $E_{pulse}$ needed to achieve the necessary conditions for micro disruption can be determined as follows:

$E_{pulse} \geq I_{threshold} \cdot \pi r^2$, where $I_{threshold}$ is the threshold intensity of the micro-disruption process.

For a tapered waveguide 62, with an output aperture having diameter 29 of 2r' the required pulse energy would likewise be determined by $E_{pulse} \geq I_{threshold} \cdot \pi r'^2$ and the tapered angle 30, α, should be less than the critical angle for total internal reflection, $$\alpha < \arcsin\left(\frac{n_2}{n_1}\right),$$

where $n_1$ and $n_2$ are the index of refraction of the waveguide material and the surroundings respectively.

For a waveguide with an angled output surface 63, of radius r, the required pulse energy would likewise be determined by $E_{pulse} \geq I_{threshold} \cdot \pi r^2 / \sin\theta$, where the tip angle 32, θ, must be greater than the critical angle for total internal reflection $$\theta > \arcsin\left(\frac{n_2}{n_1}\right).$$

For a waveguide with a conical output surface 64, of radius r having an angle 34 of θ and cone length 35 of h, the required pulse energy would likewise be determined by $E_{pulse} \geq I_{threshold} \cdot \pi r(\sqrt{h^2 + r^2})$, where the tip angle must be greater than the critical angle for total internal reflection $$\theta > \arcsin\left(\frac{n_2}{n_1}\right).$$

A curvature of the distal portion of the fiber 65 can be useful, so long as the radius of curvature 36 does not exceed mechanical limits of the fiber itself, or cause loss of light propagation due to bending losses.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entireties.

The invention claimed is:

1. An apparatus for disruption of cataracts in lens tissue enclosed by at least one of aqueous humour or vitreous humour, the apparatus comprising:
    a source of energy for emitting pulsed laser radiation, the source being controllable to select a pulsing rate of the pulsed laser radiation;
    an optical waveguide configured to transmit the pulsed laser radiation from the source to the cataracts in the lens tissue, the optical waveguide being coupleable to the source at a proximal end of the optical waveguide to receive the pulsed laser radiation from the source;
    the pulsed laser radiation being controlled to exhibit conditions at a distal end of the optical waveguide such that a light intensity which exits the optical waveguide is sufficient to produce microdisruption of the lens tissue by impulsive heat deposition, the conditions including:
        a wavelength in a range of 2700 nm to 3300 nm, the wavelength being selected to match an absorption peak of at least one component of the lens tissue;
        wherein the wavelength causes the pulsed laser radiation to produce laser pulses having an energy sufficient to cause, when the laser pulses are absorbed in a volume of material irradiated by the laser pulses, superheated temperatures above a vaporization point of at least one component of the material contained in the laser irradiated volume; and
        a pulse duration time in a range of 10 ps to 10 ns, the pulse duration time being selected such that each pulse duration time is shorter than a time required for thermal diffusion out of the laser irradiated volume and shorter than a time required for a thermally driven expansion of the laser irradiated volume to avoid shock wave propagation in the lens tissue;
    wherein the combination of selected pulse duration time and selected pulse energy is low enough to result in a peak intensity of each laser pulse below a threshold for ionization-driven ablation to occur in the irradiated material;
    wherein the conditions are selected to result in conversion of a majority of the energy contained in each laser pulse to ablation of the material in the volume with any residual energy being insufficient to substantially damage material surrounding the volume irradiated by the pulsed laser; and
    wherein, the apparatus further comprises a handle to insert and control the position of the distal end of the optical waveguide inside the lens tissue.

2. An The apparatus of claim 1 wherein the optical waveguide is an optical fiber made from an infrared-transmitting optical material.

3. An The apparatus of claim 2 wherein the optical fiber is made of a material selected from: sapphire, diamond, ZBLAN, or YAG.

4. An The apparatus of claim 2 wherein the distal end of the optical fiber is curved, tapered, conical, or angled.

5. An The apparatus of claim 2, wherein the distal end of the optical fiber is cylindrical.

6. An The apparatus of claim 1 further comprising one or more channels for irrigation and aspiration in combination and in close proximity to the distal end.

7. An The apparatus of claim 1 wherein the wavelength is selected to be 2750 nm, and wherein the pulse duration time is less than 5 ns.

8. The apparatus of claim 1, further comprising a controller, wherein the controller is configured to determine possible unwanted exposure to laser radiation based on a tracked position of the distal end of the optical waveguide relative to a three dimensional map indicating boundaries of the lens tissue,
    and the controller is further configured to reduce or cease laser radiation from the source in response to received signals indicating possible unwanted exposure to laser radiation.

9. The apparatus of claim 1, further comprising a controller, wherein the controller further receives signals from an optical sensor detecting back scattered light that is transmitted from a vicinity of the distal end of the optical waveguide to the proximal end of the optical waveguide.

10. The apparatus of claim 1, wherein the handle comprises a controller, and one or more sensors for tracking a position of the distal end of the optical waveguide inside the lens tissue; and wherein the controller is configured to send signals to the handle to cause the handle to provide a feedback based on the tracked position of the distal end of the optical waveguide.

\* \* \* \* \*